(12) United States Patent
Schuh et al.

(10) Patent No.: US 8,137,717 B1
(45) Date of Patent: Mar. 20, 2012

(54) **PRODUCTION OF HUMAN FOOD FROM *JATROPHA* AND OTHER BIOLOGICALS**

(76) Inventors: Allen John Schuh, Pleasanton, CA (US); Peter Allen Schuh, Pleasanton, CA (US)

( * ) Notice: Subject to any disclaimer, the term of this patent is extended or adjusted under 35 U.S.C. 154(b) by 327 days.

(21) Appl. No.: 12/555,696

(22) Filed: Sep. 8, 2009

(51) Int. Cl.
*A23G 3/36* (2006.01)
(52) U.S. Cl. ........................ 426/44; 435/291.5
(58) Field of Classification Search .................. 426/44; 435/291.5
See application file for complete search history.

(56) References Cited

U.S. PATENT DOCUMENTS

| | | | | |
|---|---|---|---|---|
| 4,383,040 | A | * | 5/1983 | Fricker ........................ 435/161 |
| 4,828,846 | A | * | 5/1989 | Rasco et al. ................... 426/18 |
| 2008/0040970 | A1 | | 2/2008 | Davanzo |

OTHER PUBLICATIONS

CN 101-133-780- (published Mar. 5, 2008)-English Abstract.*
CN 101-225-416- (published Jul. 23, 2008)-English Abstract.*
E. M. Aregheore et al, Detoxification of a toxic variety of *Jatropha curcas* using heat and chemical treatments, and preliminary nutritional evaluation with rats, 21 S. Pac. J. Nat. Sci. 50-56 (2003).
J. Begg et al., Main toxins Contains a purgative oil and a phytotoxin or toxalbumin curcin similar to ricin in Ricinis. *Jatropha curcas* L., National Toxicology Group, P.O. Box 913, Dunedin, New Zealand, Jun. 1994.
Environmental Control and Research Program, National Institutes of Health, Division of Occupational Health and Safety, "Phorbol esters" Safety Data Sheet, pp. 1-11, May 1984.

* cited by examiner

*Primary Examiner* — D. Lawrence Tarazano
*Assistant Examiner* — Hamid R Badr
(74) *Attorney, Agent, or Firm* — David Pressman

(57) ABSTRACT

An apparatus and process for producing humanly edible food from *Jatropha curcas* L. (JCL) or a similar plant or an algae comprises an air-tight tank (200) for containing a mixture of water, a fermenting press cake (125) of JCL seeds, yeast and other ingredients (289), including amylase and a fungus, a container for mash (290) produced during fermentation, a still (300) with a distillation column (355) for separating ethanol (360) from water, a container for ethanol (365), a source of water (215), and combustible sources (261, 296, 335) for providing heat to a plurality of burners (260, 288, 320). Ethanol produced during fermentation extracts toxic phorbol esters from the mash. After fermentation, the water and ethanol are removed from the tank and moved to the still. The mash is moved to a container (286) where it is heated to decompose toxic lectins therein, rendering the mash edible by humans and other animals. After separation in the still, the water is returned to the local source, the ethanol is saved for sale or use as a heat source for the burners, and the phorbol esters are removed from the still for safe disposal.

20 Claims, 2 Drawing Sheets

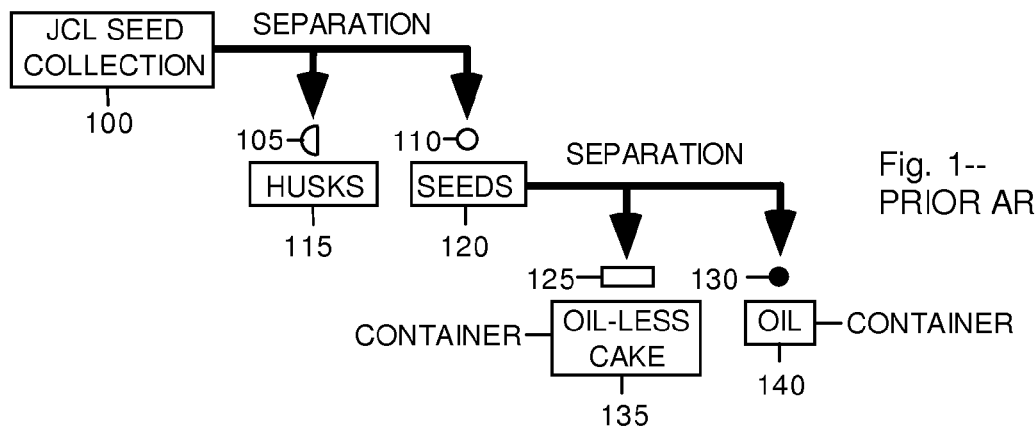
Fig. 1 -- PRIOR ART
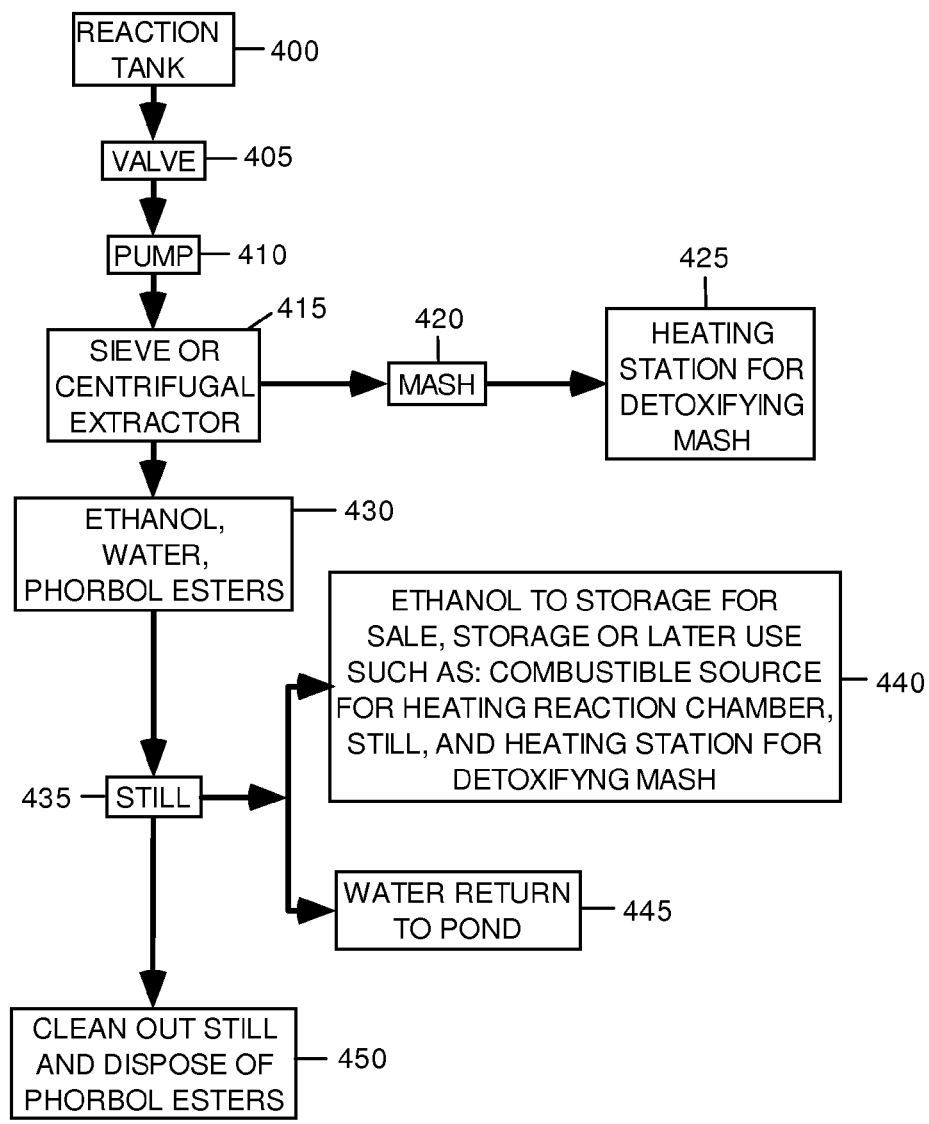
Fig. 3

PRODUCTION OF HUMAN FOOD FROM *JATROPHA* AND OTHER BIOLOGICALS

CROSS REFERENCE TO RELATED APPLICATIONS

This application is related to our applications: Ser. No. 12/399,323, filed Mar. 6, 2009, now U.S. Pat. No. 8,017,366, granted Jul. 29, 2011, and Ser. No. 12/341,380, filed Dec. 22, 2008, now U.S. Pat. No. 8,043,496, granted Oct. 25, 2011.

BACKGROUND

1. Field

The field is production and processing of biofuels.

2. Prior Art—Non-Patent Literature Documents

The following is a list of some prior art that presently appears relevant:

Begg, J. and Gaskin, T., National Toxicology Group, http://www.inchem.org/documents/pims/plant/jcurc.htm, June, 1994

Aregheore, E. M., Becker, K., and Makkar, H. P. S., "Detoxification of a toxic variety of *Jatropha curcas* using heat and chemical treatments, and preliminary nutritional evaluation with rats", S. Pac. J. Nat. Sci., 2003, Vol. 21, pp. 50-56.

Environmental Control and Research Program, National Institutes of Health, Division of Occupational Health and Safety, "Phorbol esters" Safety Data Sheet", May 1984.

Discussion

*Jatropha* is a genus of approximately 175 succulents that are perennial plants of the spurge family (Euphorbiaceae) and are native to Central and South America. "*Jatropha*" is derived from iatros (physician) and trophe (nutrition), so the plant is known by the common name "physic nut". Its seeds are used to produce *Jatropha* oil, which is burned in diesel engines, but it has other uses. The plants are resistant to drought and pests but they have poisonous components. Some varieties are deciduous, such as *Jatropha curcas* Linnaeus (JCL)

JCL is a shrub or tree that now grows pantropically. Begg and Gaskin, supra, report that the chemical composition of the seeds cultivated in common locations typically show a protein content of 18.0% by weight, fat 38.0%, and carbohydrates 17.0%. Biodiesel from JCL seeds is fast becoming recognized as a potential source of alternative fuel to meet the rising demands of countries around the world. The fuel contains no sulfur and is thus a clean, low-emission fuel. JCL has the potential to serve as fuel to power a vast array of energy needs from wheeled transportation, combined heat and power (CHP) plants, and even cooking stoves. In addition, after diesel oil is extracted, a block or cake of the plant fibers is left that can be pressed to form an oil-less cake that provides a useful agricultural material. The cake has mineral contents of nitrogen (6%), phosphorus (2.75%), and potassium (0.94%); this mineral content is similar to that of chicken manure and can be used for soil enrichment.

In addition to nutrients, the press cake contains toxic substances that give the plant its disease and pest resistance. There are two principal toxins: lectins, also known as curcin, and phorbol esters. In the past, these toxins prevented use of the press cake in human and animal nutrition.

Lectins are carbohydrate-binding proteins or glycoproteins which have specific coagulation properties. These can be broken down by heat treatments. Aregheore et al., supra, report that heat treatment inactivates lectin, reducing toxicity to tolerable levels for human consumption.

Phorbol esters are diterpenes that have tumor-promoting properties. Aregheore et al. report that the esters can be removed from the press cake by extraction using an alcohol such as ethanol. Depending upon the variety, JCL seeds contain between 0.03 and 3.3 mg of phorbol esters per gram of seeds. Neither the pressing of the seeds nor the usual prior-art processing of the oil, i.e., washing or treating with activated carbon, destroys these esters. However extraction reduces the esters to a tolerable level of 0.09 mg/g. Phorbol esters are nearly insoluble in water.

After detoxification by these two methods, humans can consume the JCL seeds and do so in some developing countries.

JCL seeds contain energy-bearing components: lipids within the seed cell structures can be collected and converted into oil used for the production of biodiesel according to procedures described elsewhere (see our above U.S. Pat. No. 8,043,496); carbohydrates in the cell structures can be converted into sugars and then ethanol, which is used first to scrub the press cake to be detoxified and then the same ethanol is used to process the oil to be biodiesel by procedures as described elsewhere (see our above U.S. Pat. No. 8,017,366). After removing the oil and the ethanol used in extraction of toxins, the protein meal is suitable for human consumption. The husks of JCL fruits amount up to 35% of the weight of the fruit and at harvest the dry husks can be directly used as a fuel.

When JCL is grown in hedges or in small farms in developing countries, the yield of fruit, i.e., JCL nuts and their husks, is about 1 kg/sq. meter/year, thereby limiting oil generation to a local enterprise. Collecting and processing the fruit can provide needed fuel, and can also inject money into the local economy. The added ability of producing a protein-rich meal for consumption enhances the potential of JCL as an economically viable feedstock.

Insofar as we are aware, there no transportable processing apparatus that can be delivered along a water course by ship or barge, by rail line, by road wheeled transportation, or by air to a location in proximity to the agricultural sites where JCL is grown.

SUMMARY

A portable apparatus can convert JCL and similar seeds into humanly edible food and biofuel at the village level and it can accomplish those tasks in a short period of time. This apparatus may be utilized 24 hours/day and 365 days per year by sharing it among agricultural settings. The apparatus is simple and logical in construction, utilizes self-generated fuel, and utilizes important human engineering principles for operation and maintenance of the apparatus in a safe manner by a single person. A single container having about a 2,000 liter capacity and ability to withstand temperatures of at least 133 deg. C. is required. The container is a reactants tank for ethanol production and oil-less cake detoxification.

DRAWING FIGURES

FIG. 1 is a diagram illustrating a prior-art process for extracting oil from JCL and similar seeds.

FIG. 3 is a block diagram illustrating alternative methods of separating the solids from the liquids in the reaction tank of FIG. 2.

Figure 2:
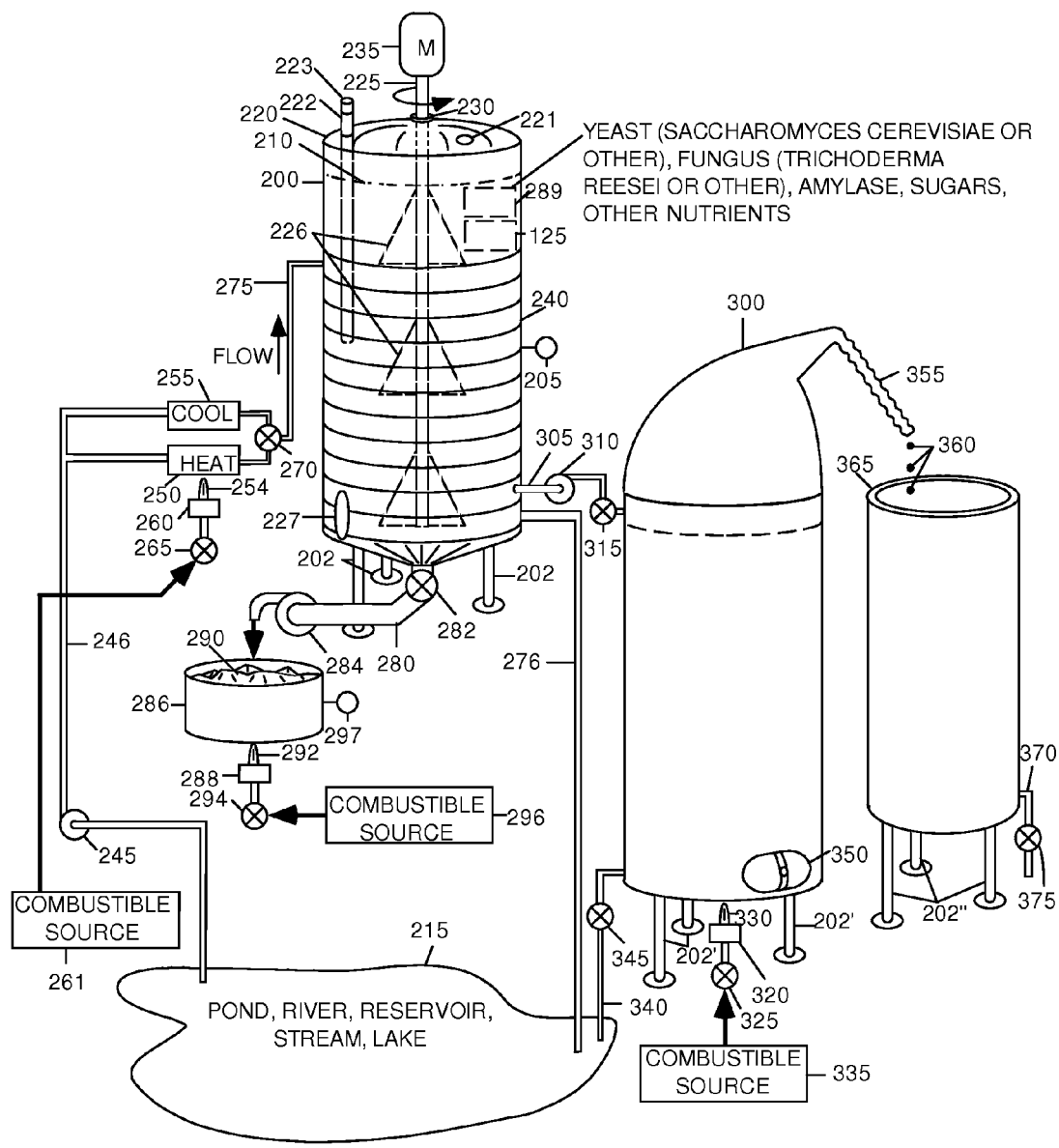
FIG. 2 is a schematic diagram of one apparatus for detoxifying a JCL seed cake.

| DRAWING FIGURE REFERENCE NUMERALS | | | |
|---|---|---|---|
| 100 | Station | 105 | Husks |
| 110 | Seeds | 115 | Container |
| 120 | Container | 125 | Cake |
| 130 | Oil | 135 | Container |
| 140 | Container | 200 | Tank |
| 202 | Leg | 205 | Sensor |
| 210 | Level | 215 | Water source |
| 220 | Lid | 221 | Airlock |
| 222 | Tube | 223 | Cap |
| 225 | Shaft | 226 | Paddles |
| 227 | Sight glass | 230 | Seal |
| 235 | Motive source | 240 | Blanket |
| 245 | Pump | 246 | Conduit |
| 250 | Heat exchanger | 254 | Flame |
| 255 | Cooling station | 260 | Burner |
| 261 | Source | 265 | Valve |
| 270 | Valve | 275 | Conduit |
| 276 | Conduit | 280 | Conduit |
| 282 | Valve | 284 | Pump |
| 286 | Container | 288 | Burner |
| 289 | Yeast | 290 | Mash |
| 292 | Flame | 294 | Valve |
| 296 | Source | 297 | Sensor |
| 300 | Still | 305 | Conduit |
| 310 | Pump | 315 | Valve |
| 320 | Burner | 325 | Valve |
| 330 | Flame | 335 | Source |
| 340 | Conduit | 345 | Valve |
| 350 | Port | 355 | Column |
| 360 | Droplets | 365 | Container |
| 370 | Conduit | 375 | Valve |

PREVIOUS PREPARATION OF REACTANTS

FIG. 1—Prior Art

Heretofore JCL and similar seeds in their husks were processed for collection of their oil for use in biofuels by first delivering them to a collection station 100 (FIG. 1). Next the husks 105 and seeds 110 were separated manually, through a sieve, or by another method. Husks 105 were placed into a container 115. Seeds 110 were placed into a container 120 prior to a second separation operation, usually comprising pressing seeds 110 (not shown) into an oil-less cake 125 that is stored in a container 135. The oil 130 stored in a container 140. A typical cake has a granular paste texture and weight and volume of approximately 25 kilograms and 20 liters, respectively.

Preferred Embodiment for First Process

Production of Ethanol—Description—FIG. 2

Since cake 125 contain toxins, it is not fit for human and animal consumption. According to this embodiment, two process steps are used to detoxify it. These are the extraction of phorbol esters and heating of the cake to inactivate lectins. A third step refines ethanol produced in the first step and uses it for various purposes, including providing heat for use in the first two steps.

In a first process step, phorbol esters are extracted from cake 125 using ethanol. FIG. 2 is a schematic diagram of one apparatus for performing this step. The apparatus comprises a tank 200 that holds a mixture of reactants and reaction products and is supplied with various instruments and controls. The reactants include cake 125 and water up to a level 210 that is derived from a local source, such as a pond, river, reservoir, stream, lake, or the like 215. Level 210 is at approximately 90 percent of the height of tank 200, although other heights can be used as appropriate. Cake 125 is shown near level 210; however once immersed in tank 200, cake 125 dissolves and is dispersed throughout tank 200. Cake 125 and other reactants are introduced into tank 200 prior to emplacement of lid 220 or through a sealable opening such as tube 222 and cap 223. Tank 200 is preferably made of a non-reactive metal, such as stainless steel, and has a capacity of 2,000 liters; however larger or smaller volumes can be used. It is supported and leveled by a plurality of legs 202.

Tank 200 has a sealed, domed lid 220. An airlock 221 permits gas to escape from tank 200, but prevents entrance of air during operation. Airlock 221 can be a simple check valve or flapper valve oriented to permit release of gas from tank 200. A shaft 225 with attached paddles 226 passes through a seal 230 in lid 200. Shaft 225 is connected to a motive source 235. Source 235 is any source of rotation that can periodically turn shaft 225, such as a hand crank, electric motor, internal combustion engine, water wheel, or the like.

Tank 200 is wrapped with an optional thermal blanket 240. In certain climates and locations, blanket 240 is not required since local temperatures maintain tank 200 at the desired temperature for fermentation of the feedstock contained therein. Blanket 240 preferably comprises a set of tubes through which hot or cold water can be passed in order to maintain a predetermined temperature within container 200.

A pump 245 supplies water from pond 215 to a heat exchanger 250 and a cooling station 255 via a conduit 246. Cooling station 255 can be cooled by an evaporative spray or other means (not shown), or simply by passage through of water from pond 215. Heat exchanger 250 is heated by a flame 254 from a burner 260. Burner 260 is fueled by burning husks 105 (FIG. 1), or flammable gas or fluid from any combustible source 261. Alternatively, burner 260 can be replaced by a resistive electric heater (not shown), or a source of solar or geothermal heat (not shown).

A valve 265 adjusts the flow of flammable fluid or gas to burner 260. Water exits heat exchanger 250 and cooling station 255 via a proportional valve 270. Valve 270 is arranged to pass either heated or cooled water or a mixture of the two to blanket 240 via a conduit 275. The water passing through blanket 240 exits via a conduit 276 and is returned to pond 215. The temperature within tank 200 is monitored by a temperature sensor 205. Valves 265 and 270 can be manually operated or powered by external motive forces (not shown).

A tube 222 with a sealing cap 223 extends through lid 220 to about one half the height of tank 200. Tube 222 permits sampling and adjusting the contents of tank 200. Variables such as toxin level, nutrient content, pH (an acid-base measure), amount of ethanol present, and the like can be monitored through tube 222 in order to optimize the chemical reactions in tank 200. A sight glass 227 is located near the bottom of tank 200 for later inspection of the contents.

Tank 200 further includes an outlet conduit 280, a normally-closed valve 282, and an optional pump 284. The outlet of conduit 280 is positioned over a container 286. Opening valve 282 and energizing optional pump 284 causes the contents of tank 200, referred to as mash, to be deposited into container 286. A burner 288 is positioned beneath container 286 and mash 290. Burner 288 supplies a flame 292 to heat container 286 and mash 290. A temperature sensor 297 indicates the temperature of the contents of container 286. Burner 288 is supplied by a combustible source 296 and the size of flame 292 is adjusted by a valve 294. Source 296 is supplied by any of the possible combustibles available to source 261.

Tank 200 is connected to a still 300 via a conduit 305, a valve 315, and optional pump 310. If present, pump 310 can be powered manually, electrically, or by other means. Still 300 is preferably supported on a plurality of legs 202'. If still 300 is positioned below tank 200 as shown, pump 310 is not required since opening valve 315 will permit the contents of tank 200 to flow into still 300 by gravity. The volume of still 300 is approximately the same as that of tank 200 so that the liquid contents of tank 200 can be moved into still 300 at a predetermined time.

A second burner 320 with an adjusting valve 325 is arranged to heat still 300. Burner 320 is supplied with a combustible source 335 that can provide the same or a different combustible material than that supplied by source 281.

Still 300 further includes an outlet conduit 340 and valve 345. To drain still 300, valve 345 is opened and the contents of still 300 flow into pond 215. A clean-out port 350 is located near the bottom of still 300. After most of the fluid contents of tank have been drained, port 350 is opened to permit removal of any solid or semi-solid contents that have settled to the bottom of still 300.

A condensing column 355 is positioned at the top of still 300. During operation of still 300, distillation vapors condense within column 355 and flow downward, as indicated by droplets 360. A container 365 is positioned beneath column 355 and receives droplets 360. Container 365 is preferably supported on a plurality of legs 202", although another support can be used, if desired. The volume of container 365 is determined by the fraction of liquid within still 300 that will be distilled. Typically, the volume of container 365 is about half that of still 300, although other sizes or a plurality of containers can be used. Container 365 further includes an outlet conduit 370 and a normally-closed valve 375. Valve 375 is opened when it is desired to drain the contents of container 365.

Preferred Embodiment for First Part of Process

Partial Detoxification of the Press Cake—Operation—FIGS. 1 and 2

The phorbol esters initially present in cake 125 (FIG. 1) are extracted using ethanol derived in part from cake 125. Tank 200 is prepared for the first process by draining all previously contained substances and cleaning, if necessary.

Next, with lid 220 open, the following ingredients are added to tank 200: a press cake 125 having a volume of approximately 1,200 liters, 600 liters of water, one liter of a fungus, preferably *Trichoderma reesei*, often obtained from the roots of local plants. This fungus is used in enzyme production during fermentation.

Also one liter of amylase is added. Amylase is an enzyme that breaks starch into sugar and is commonly used in the brewing industry to break down carbohydrates. Other yeasts, fungi, and substitutes for amylase are well-known and can be used if the preferred substances are not locally available.

Further a cake 289 containing one liter of an alcohol-producing yeast, preferably *Saccharomyces cerevisiae* yeast is added.

The above volumes are typical; however other volumes can be used. The amounts can be varied to optimize the process given local temperatures and other conditions such as acidity of the water, the local variety of JCL and its peculiar chemical composition, and the like.

Although tank 200 has a volume of 2,000 liters, it is only filled to 90% of its capacity or 1,800 liters at level 210 in order to prevent overflow through airlock 221 during the fermentation process. Additional sugars and nutrients (not shown) can be added at this time to regulate the production of ethanol. They can also be added at a later time through tube 222, as required.

Next, lid 220 is closed and sealed and cap 223 is secured on tube 222. Air must be excluded from tank 200 since in the presence of oxygen, the yeast in cake 289 will undergo aerobic respiration and produce carbon dioxide and water, rather than ethanol. The production of ethanol commences immediately as press cake 125 and yeast cake 289 dissolve.

After lid 220 is closed, motive source 235 is temporarily activated to disrupt and dissolve the contents of tank 200 and form a feedstock slurry comprising the contents of cakes 125 and 289 and the water. Motive source 235 is periodically activated during the reaction to cause paddles 226 to stir the contents of tank 200 and optimize ethanol production by bringing the yeast into contact with sugars, both those present in cake 125 and those sugars and nutrients optionally added to the mixture. As the reaction between the yeast and the sugars present in the mixture in tank 200 proceeds, $CO_2$ is produced and allowed to escape through airlock 221.

The production of ethanol is a relatively low-temperature operation. The contents of tank 200 must be kept at approximately 32±2° C. in order to maximize the growth rate of the particular strain of yeast in cake 289, which in the present example is *S. cerevisiae*. Pump 245 is activated as necessary, drawing water from pond 215 and circulating it through heat exchangers 250 and 255, blanket 240, and conduit 276. The required temperature range is maintained manually by a human operator who observes the temperature indication on sensor 205 and then adjusts valves 265 and 270 accordingly to increase or decrease the temperature of blanket 240 and hence tank 200. Alternatively, an automatic system (not shown) can be arranged to provide the same control over temperature within tank 200. In tropical climates, it may become necessary to shade tank 200 and its associated components from exposure to the sun in order not to exceed the required 32° C.

The rate of production of ethanol gradually accelerates, peaks, and then declines over the production cycle. Ethanol production is allowed to continue until the operator determines that there has been sufficient conversion of the feedstock, usually by sampling through tube 222. The process may be substantially complete in two days.

The ethanol thus produced in tank 200 extracts the phorbol ester that was initially present in cake 125. The ester remains in solution in the ethanol. Additional ethanol can be added from an external source (not shown) to extract additional phorbol ester, if necessary.

After approximately two days, when the ethanol production is substantially completed, as determined by sampling the contents of tank 200 through tube 222, airlock 221 is opened and the second phase of detoxification of the contents of cake 125 commences.

Second Part of Process—Final Detoxification of Press Cake—Description and Operation—FIG. 2

After the production of ethanol, the stifling of the contents of tank 200 is stopped and the solids comprising mash 290 in the mixture are allowed to settle to the bottom of tank 200. When mash 290 has substantially settled, as verifiable by inspection through sight glass 227, valve 315 is opened and the remaining liquid contents of tank 200, comprising mainly ethanol, phorbol esters, and water, are urged to flow from tank 200 to still 300. If the bottom of tank 200 is positioned above the top of still 300, pump 310 is not necessarily required since the fluids in tank 200 will flow into still 300 under the urging of gravity. Otherwise, pump 310 is used to move the fluids from tank 200 to still 300 via conduit 305.

Next, valve 282 is opened and mash 290 is permitted to flow from tank 200 into container 286. If container 286 is located above the bottom of tank 200, or if mash 290 is very thick, pump 284 is used to draw mash 290 through conduit 280.

Next, burner 288 is activated to heat mash 290 by flame 292. The level of heat supplied to the bottom of container 286 is regulated by valve 294. Source 296 is supplied with any of the same combustible materials as source 261. Mash 290 is stirred while it is heated to facilitate drying. After any remaining water and ethanol have evaporated, the temperature of mash 290 increases and will eventually reach 133° C., as verified by temperature sensor 297, thereby destroying all lectins present and rendering mash 290 suitable for human consumption. The dried and thermally processed mash 290 ("cake") has the consistency of ordinary bread.

Third Part of Process—Distilling Ethanol Produced in Step 1—Description and Operation—FIG. 2

The ethanol produced in step 1 is valuable and easily separated both from the water in which it is dissolved and the phorbol esters which are dissolved in the ethanol.

After fermentation, the liquid contents of tank 200 were moved into still 300. Most of the phorbol esters have been extracted from mash 290 and are presently dissolved in the ethanol that was produced during fermentation of yeast cake 289 and cake 125.

Still 300 is activated by lighting burner 320. Burner 320 is supplied with a combustible source material 335 that passes through a regulator valve 325. Source 335 provides any of the same combustible materials that are made available to sources 261 and 296.

As still 300 is heated, the ethanol is preferentially distilled from the water, leaving behind water and phorbol esters. At sea level, ethanol and water boil at 78.3° C. and 100° C., respectively. The optimum temperature for distillation of the ethanol from the water depends upon the relative fraction of the two components. In general, a temperature between the above two is used. Phorbol esters have a much higher melting point of approximately 200° C. and their volatility is considered to be negligible. Thus, as the ethanol leaves the mixture in still 300, the phorbol esters and water are left behind.

Phorbol esters are nearly insoluble in water and their molecular weight is greater than that of water. When still 300 is allowed to return to ambient temperature, all convective stirring will stop and esters will settle to the bottom of still 300. When still 300 is cooled to ambient temperature and the phorbol esters have settled to the bottom, valve 345 is opened and the water remaining in still 300 is drained through conduit 340 back into pond 215. At this point, clean-out opening 350 is opened and the phorbol esters are removed from still 300. Because of their toxic and mutagenic properties, great care must be exercised in this removal step and the esters must be disposed of safely.

When valve 375 is opened, the ethanol in container 365 is drained through conduit 370. The ethanol is suitable for use as a combustible source, or it can be sold, stored, or used in the production of biodiesel.

After heating in container 286, the final edible product is spooned or scraped out into a container (not shown) suitable for storage or even consumption. It is rich in nutrients and protein and relatively low in carbohydrates and fats. It has the flavor and texture of soy meal and can be used as a substitute for soy meal in various recipes, including pastry, desserts, soups, salads, or as a main course. It can be flavored with various ingredients, such as cinnamon and the like.

Although the above disclosure relates to JCL, other feedstocks can be used. I believe that any plant with a toxin that can be detoxified by alcohol or heat, or both, can be successfully treated with this apparatus and methodology and then safely eaten. Such feedstocks include castor beans (*Ricinus communis*), jojoba beans (*Simmondsia chinensis*), Indian beech (*Pongamia pinnata*), and even algae, including toxic marine algae. Additional feedstocks mentioned above include amylase, fungi, and sugars.

Alternative Embodiment

Separation of Mash and Liquids—FIGS. 2 and 3

Instead of draining tank 200 after fermentation as described above, the solids in tank 200 can be separated from the liquids by a well-known sieve or centrifugal extractor. These methods are useful when cake 125 is very finely divided and the after-fermentation settling time in tank 200 would be prohibitively long.

FIG. 3 shows a block diagram of these alternative methods of separation as they are incorporated into the first embodiment. Reaction tank 200 still terminates in conduit 280, valve 282, and optional pump 284 (FIG. 2). The original reactants are added to tank 200 and allowed to ferment, as described above (block 400). After fermentation is complete, valve 405 is opened and optional pump 410 is activated (blocks 405 and 410), delivering the contents of tank 200 to a sieve or centrifugal extractor (block 415). The sieve or extractor separates the mash from the liquid (block 420) and delivers it to heating station container 286 (block 425) where the mash is cooked and the lectins decompose. The ethanol, water, and phorbol esters (block 430) are delivered to still 300 (block 435) where they are processed as described above, i.e., the ethanol is distilled (block 440), the remaining water is returned to pond 215 (block 445), and the still is cleaned (block 450).

CONCLUSIONS, RAMIFICATIONS, AND SCOPE

As we have shown we have devised a system and method for the production of humanly edible food from JCL and other feedstocks. A by-product of the process is ethanol that can be used for production of additional cake, and for a variety of other uses, including chemical conversion into biodiesel.

In the case of JCL, the feedstock is purged of two primary toxins, phorbol esters and lectin, and delivered to the end consumer as a dried cake. During the process, the lectin decomposes, while the phorbol esters are collected for safe disposal.

Numerous variations of reactants and apparatus can be used. Instead of *S. cerevisiae*, another alcohol-producing yeast can be used. Instead of *T. reesei*, another fungus can be used. Tank 200 can be made of plastic, wood, ceramics, fiberglass, and other materials. Still 300 can be made of any non-reactive material that can withstand heating during distillation of the ethanol from the water. Container 365 can be a rigid container or a sturdy bag. The sizes of the components and the quantities of the chemicals and reactants employed can be varied.

While the present system employs elements which are well known to those skilled in the arts of biomass conversion design, it combines these elements in a novel way which produces new results not heretofore discovered. Accordingly the scope of this invention should be determined, not by the embodiments illustrated, but by the appended claims and their legal equivalents.

The invention claimed is:

1. An apparatus for producing humanly-edible food cake from a feedstock comprising water, yeast, fungi, amylase, sugars, and a biological containing a first toxin that can be rendered harmless by heating and a second toxin that is soluble in alcohol, said biological selected from the group consisting of algae, castor beans, jojoba beans, Indian beech seeds, and *Jatropha curcas* L. seeds, said apparatus comprising:
- (a) an air-tight fermenting tank with a stirrer, said stirrer driven by a motive source, said fermenting tank being arranged to anaerobically ferment said feedstock into a mixture comprising at least a plurality of components selected from the group consisting of mash, ethanol, water, a first toxin that can be rendered harmless by heating, and an ethanol-soluble second toxin,
- (b) a still,
- (c) a heating container, and
- (d) a first conduit with a normally-closed first valve that connects said fermenting tank to said still, thereby permitting the liquid part of said components in said tank to flow from said fermenting tank into said still when said first valve is open,
- (e) said fermenting tank further including a normally-closed second valve and a second conduit for delivering said mash to said heating container when said second valve is open,
- (f) said still having a first heater arranged to heat the contents of said still to distill ethanol from said liquid component,
- (g) said heating container having a second heater and being arranged to heat said mash and said first toxin, thereby rendering said first toxin harmless and producing said cake,
- whereby said apparatus will be able to reduce the amount of said first and said second toxins in said mash sufficiently to render said cake safe for human and animal consumption and also produce alcohol.

2. The apparatus of claim 1, further including an apparatus connected to said tank, said apparatus being selected from the group consisting of a water jacket, a heat exchanger, and a temperature sensor.

3. The apparatus of claim 1 wherein said motive source is selected from the group consisting of hand cranks, electric motors, internal combustion engines, and water wheels.

4. The apparatus of claim 1, further including plurality of openings in said tank, said opening being selected from the group consisting of sealable openings and airlocks.

5. The apparatus of claim 1, further including a sieve connected to said first conduit.

6. The apparatus of claim 1, further including a centrifugal extractor connected to said first conduit.

7. The apparatus of claim 1 wherein said first heater is arranged to heat said still to cause ethanol in said still to be distilled from said contents of said still, whereby said ethanol can be placed into a second container for storage.

8. A method for producing humanly-edible food cake from a feedstock comprising water, yeast, fungi, amylase, sugars, and a biological containing a first toxin that can be rendered harmless by heating and a second toxin that is soluble in alcohol, said biological selected from the group consisting of algae, castor beans, jojoba beans, Indian beech seeds, and *Jatropha curcas* L. seeds, comprising:

providing a feedstock, providing a source of water, providing an air-tight fermenting tank with a stirrer, said stirrer driven by a motive source, said fermenting tank being arranged to anaerobically ferment said feedstock into a mixture comprising at least components selected from the group consisting of mash, ethanol, water, and said first and said second toxins, providing a still with a first heater, providing a first container arranged to receive distillates from said still, providing a second container with a second heater, adding said feedstock to said fermenting tank, periodically energizing said motive source so as to disperse the contents of said fermenting tank, permitting said contents of said tank to ferment and form a mash, thereby producing ethanol that extracts said second toxin from said mash, after fermentation, moving said water, said ethanol, and said second toxin from said fermenting tank to said still and moving said mash to said second container, energizing said second heater and heating said mash in said second container to a temperature sufficient to decompose said first toxin, and energizing said first heater on said still, thereby distilling said ethanol from said water and causing said ethanol to be conveyed into said first container, whereby said mash is delivered to said second container and heated using said second heater so that the amount of said first and said second toxins in said mash is reduced sufficiently to render said cake safe for human and animal consumption, and alcohol will be produced.

9. The method of claim 8 wherein said fermenting tank has a lid and said lid of said tank includes a plurality of openings selected from the group consisting of sealable openings and airlocks.

10. The method of claim 8 wherein said motive source is selected from the group consisting of hand cranks, electric motors, internal combustion engines, and water wheels.

11. The method of claim 8 wherein said fermenting tank has a water jacket.

12. The method of claim 11 wherein said water jacket has a heat exchanger.

13. The method of claim 8 wherein each of said heaters is supplied with combustible sources.

14. The method of claim 8 wherein said source of water is selected from the group consisting of ponds, rivers, reservoirs, streams, and lakes.

15. The method of claim 8 wherein said mash is separated from said ethanol, said phorbol esters, and said water by apparatus selected from the group consisting of sieves and centrifugal extractors.

16. An apparatus for producing a humanly-edible food cake from a feedstock comprising water, yeast, fungi, amylase, sugars, and a biological containing a first toxin that can be rendered harmless by heating and a second toxin that is soluble in alcohol, said biological selected from the group consisting of castor beans, jojoba beans, Indian beech seeds, algae, and *Jatropha curcas* L. seeds, comprising:

an air-tight fermenting tank with stifling means, said stirring means driven by a motive source, said fermenting tank being arranged to anaerobically ferment said feedstock into a mixture comprising at least components selected from the group consisting of mash, ethanol, water, a first toxin that can be rendered harmless by heating, and an ethanol-soluble second toxin, a still having a first heating means arranged to heat the contents of said still, a heating container having a second heating means arranged to heat the contents of said container, said fermenting tank further including a normally-closed valve and a first conduit for delivering said mash to said heating container when said valve is open, a second conduit with a normally-closed valve that connects said fermenting tank and said still, thereby permitting the liquid component in said tank to flow from said fermenting tank into said still when said valve is open, said still being arranged to distill ethanol from said liquid component, said heating container being arranged to heat said mash and said toxin, thereby rendering said toxin harmless and producing said cake, whereby said apparatus will be able to reduce the amount of said first and said second toxins in said mash sufficiently to render said cake safe for human and animal consumption and also produce alcohol.

17. The apparatus of claim 16 wherein said motive source is selected from the group consisting of hand cranks, electric motors, internal combustion engines, and water wheels for powering said stirring means.

18. The apparatus of claim 16, further including a plurality of openings in said fermenting tank selected from the group consisting of sealable openings and airlocks.

19. The apparatus of claim 16, further including a sieve connected to said first conduit.

20. The apparatus of claim 16, further including a centrifugal extractor connected to said first conduit.

* * * * *